US00PP20362P2

(12) United States Plant Patent
Snoeijer

(10) Patent No.: US PP20,362 P2
(45) Date of Patent: Sep. 29, 2009

(54) ***CLEMATIS* PLANT NAMED 'ZOKLAKO'**

(50) Latin Name: ***Clematis* hybrid**
Varietal Denomination: Zoklako

(76) Inventor: Wim Snoeijer, Vest 162, 2801 TX Gouda (NL)

( * ) Notice: Subject to any disclaimer, the term of this patent is extended or adjusted under 35 U.S.C. 154(b) by 0 days.

(21) Appl. No.: 12/228,015

(22) Filed: Aug. 8, 2008

(51) Int. Cl.
*A01H 5/00* (2006.01)

(52) U.S. Cl. ..... Plt./228

(58) Field of Classification Search ..... Plt./228
See application file for complete search history.

(56) References Cited

OTHER PUBLICATIONS

Upov-rom Plant Variety Database 2009/01, GTI Jouve Retrieval Software, Citation for *Clematis* 'Zoklako', one page.*

* cited by examiner

*Primary Examiner*—June Hwu
(74) *Attorney, Agent, or Firm*—Penny J. Aguirre

(57) ABSTRACT

A new cultivar of hybrid *Clematis*, 'Zoklako', characterized by its star-shaped upright facing flowers that exhibit purple margins and white centers with purple veins and stamens comprised of purple filaments and yellow anthers, its free flowering habit in spring with additional flowering in summer and early fall, its climbing growth habit, and its cold hardiness to U.S.D.A. Zone 6.

3 Drawing Sheets

Botanical classification: *Clematis* hybrid.
Variety denomination: 'Zoklako'.

CROSS REFERENCE TO A RELATED APPLICATION

This application is co-pending with a U.S. Plant Patent applications filed for a sibling derived from the same seedlot entitled *Clematis* Plant Named 'Zodaque' (U.S. Plant Pat. application Ser. No. 12/228,035).

BACKGROUND OF THE INVENTION

The present invention relates to a new and distinct cultivar of *Clematis*, botanically of hybrid origin and classified in the Patens Group, and will be referred to hereafter by its cultivar name, 'Zoklako'. 'Zoklako' is grown as an herbaceous climber for landscape use and for use as a flowering potplant for the terrace.

'Zoklako' was selected as unique amongst a group of seedlings that the inventor grew for evaluation in his nursery in Boskoop, The Netherlands. The goal of the selection was to select a hardy climber with uniquely colored flowers that could be grown for different purposes in the garden. 'Zoklako' was selected by the inventor in summer of 2002 and derived from seeds collected in 1999 and sown in 2000 from open pollinated *Clematis* 'Silver Moon' (not patented).

Asexual reproduction of the new cultivar was first accomplished by internodial stem cuttings under the direction of the inventor in Boskoop, The Netherlands in 2003. The characteristics of this cultivar have been determined to be stable and are reproduced true to type in successive generations.

SUMMARY OF THE INVENTION

The following traits have been repeatedly observed and represent the characteristics of the new cultivar as grown outdoors 'Zoklako' from other cultivars of *Clematis* known to the inventor.

1. 'Zoklako' exhibits upright flowers that are unique in color with purple margins and white centers with purple veins and stamens comprised of purple filaments and yellow anthers.
2. 'Zoklako' is free flowering in spring with additional flowers produced throughout the summer into early fall.
3. 'Zoklako' exhibits a climbing growth habit.
4. 'Zoklako' is cold hardy to U.S.D.A. Zone 6. 'Zoklako' differs from its female parent in that 'Silver Moon' has flowers with wide purple margins with lighter purple centers and bright yellow stamens. 'Zoklako' differs from its sibling selection, 'Zodaque', in flower color and in having single flowers. 'Zodaque' has semi-double flowers that are pale purple in color. Close comparisons are *Clematis* 'Ivan Olsson' and 'Omoshiro' (both unpatented). 'Ivan Olsson' differs from 'Zoklako' in having flowers that are violet-blue with white centers rather than purple with white centers, in having with tepals that are more rounded and in having stamen connectives that are red-purple rather than yellow. 'Omoshiro' differs from 'Zoklako' in having flowers that are white with a red-purple hue and a thin red margin, tepals that are more rounded and stamen connectives that are red-purple rather than yellow.

BRIEF DESCRIPTION OF THE DRAWING

The accompanying colored photographs illustrate the overall appearance and distinct characteristics of the new *Clematis*. The photographs were taken of a plant of 'Zoklako' as grown in a trial bed for 3 years in Boskoop, The Netherlands.

Figure 1:
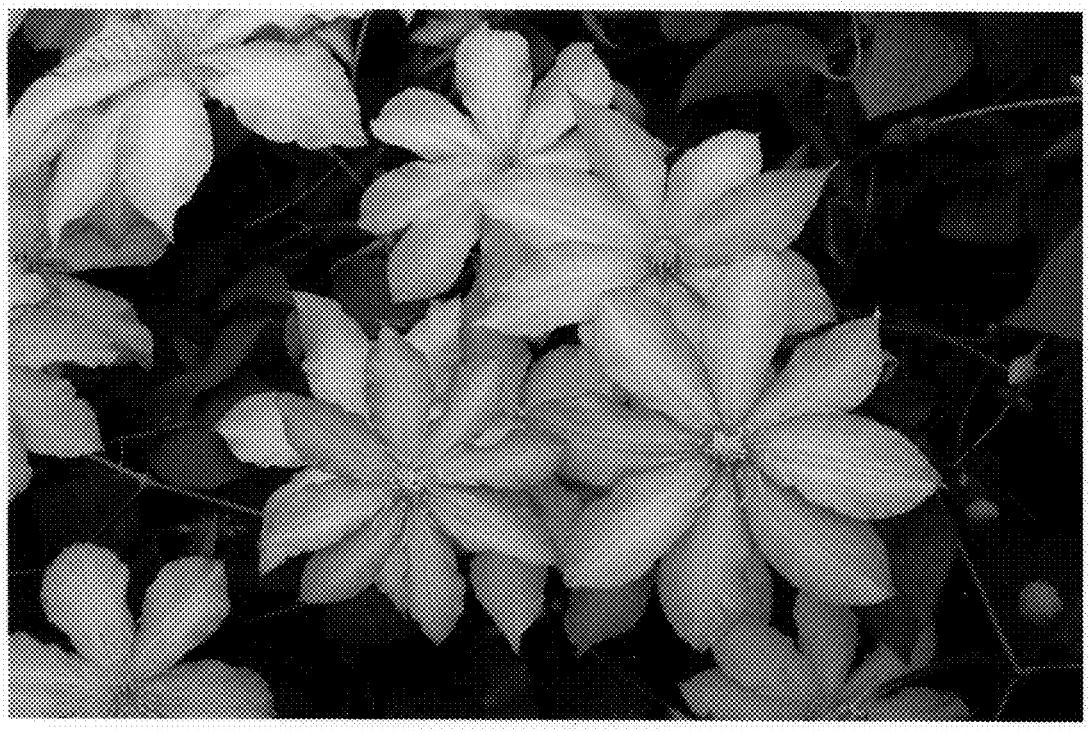
FIG. 1 shows the flowering habit.
Figure 2:
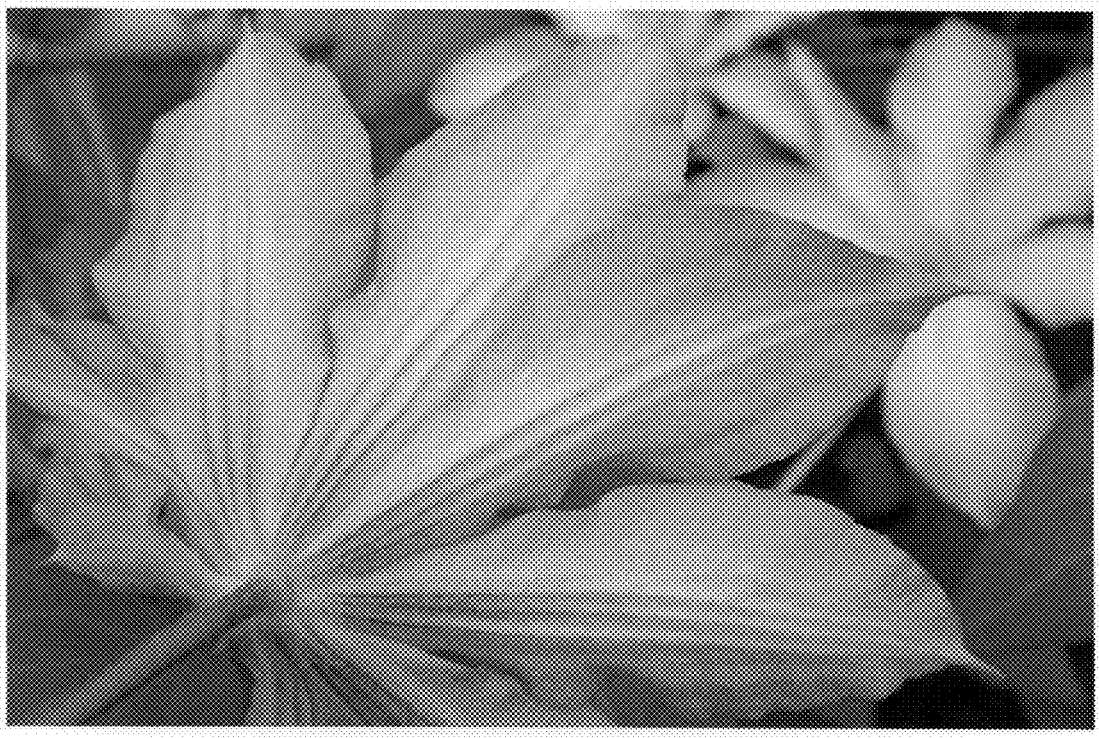
FIG. 2 provides a close-up view of the lower surface of the flower.
Figure 3:
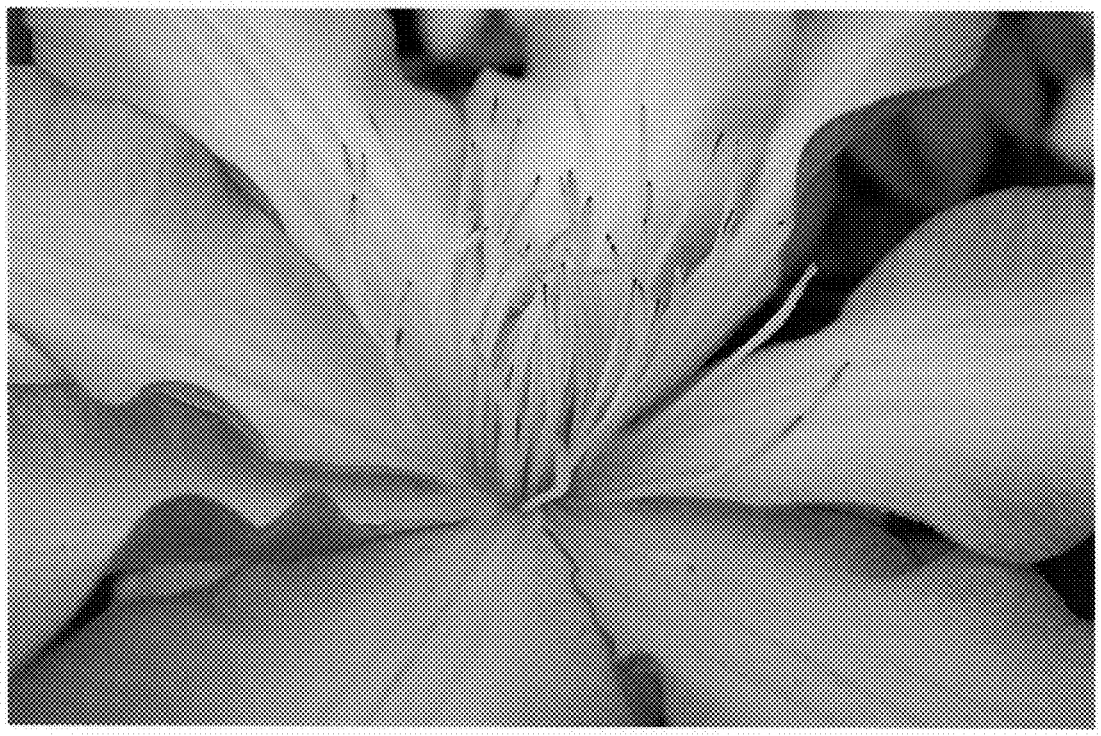
FIG. 3 provides a close-up view of the upper surface of the flower and stamens.
Figure 4:
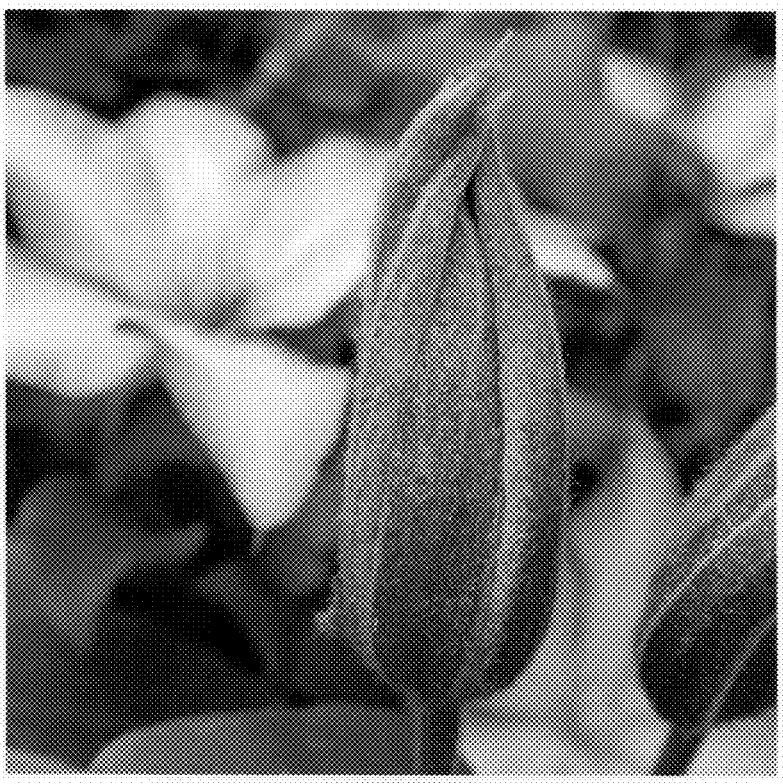
FIG. 4 provides a view of a flower bud.
Figure 5:
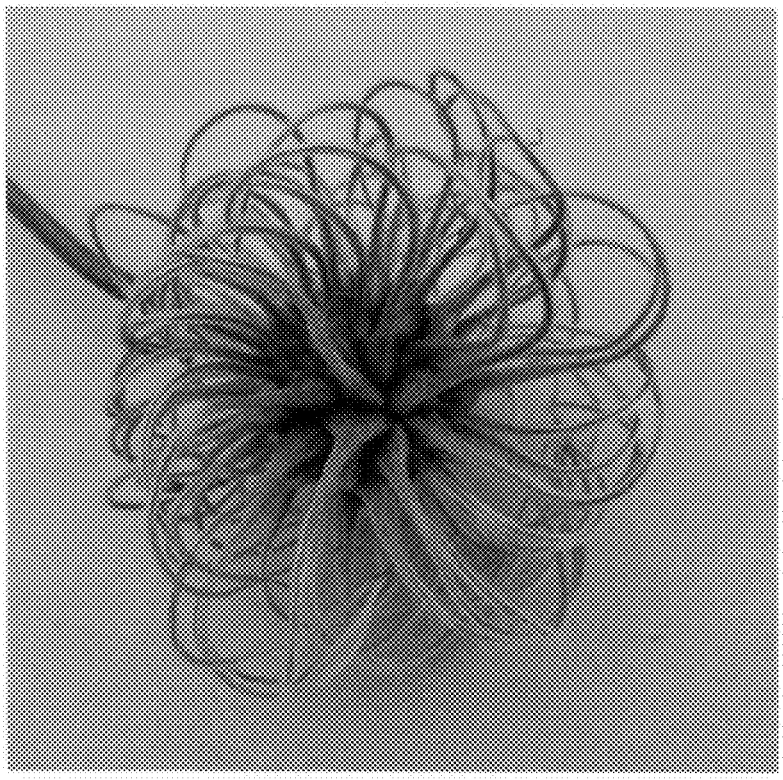
FIG. 5 provides a close-up view of a seedhead.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of 3 year-old plants of 'Zoklako' as grown outdoors in full sun to semi-shade in a test plot in Boskoop, The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Zoklako' is classified in the Patens Group of *Clematis*.

*Blooming period.*—Free flowering for 4 weeks to 6 weeks in spring with additional flowers produced throughout the summer into early fall.

*Plant habit.*—Herbaceous climber.

*Height and spread.*—Three year-old plant is about 15 cm at base with a height of about 2 m when pruned after spring flowering.

*Cold hardiness.*—U.S.D.A. Zone 6.

*Culture.*—Moist but well-drained soils in full sun with roots shaded.

*Diseases.*—No particular resistance to diseases has been observed.

*Root description.*—Fleshy.

Growth and propagation:

*Propagation.*—Internodial softwood cuttings from vegetative shoots.

*Root initiation.*—Roots develop in 6 weeks in summer under greenhouse conditions.

*Time required for root development.*—75 to 90 days to develop a 5 cm container from a 5 cm cutting.

*Growth rate.*—Moderately vigorous once planted in the landscape.

Stem description:

*Shape.*—Round and 6 ribbed.

*Stem color.*—Emerges 59C, matures to 178B.

*Stem size.*—About 2 m (including peduncle and terminal pedicel) in length, average of 5 mm in diameter.

*Stem surface.*—Sparsely covered with hairs.

*Internode length.*—Ranges from 7 to 15 cm.

*Branching.*—Basal branching.

Foliage description:

*Leaf arrangement.*—Opposite.

*Leaf division.*—Ternate.

*Leaflet shape.*—Broadly lanceolate.

*Leaflet base.*—Cuneate.

*Leaflet apex.*—Acuminate.

*Leaflet fragrance.*—None.

*Leaflet venation.*—Primarily reticulate, not prominent, 144C in color.

*Leaflet margins.*—Entire.

*Leaflet attachment.*—Petioluled with leaf petioled.

*Leaflet surface.*—Upper surface glabrous with veins sparsely covered with hairs, lower surface is sparsely covered with hairs.

*Leaflet size.*—Up to 11 cm in length and 6 cm in width.

*Leaflet color.*—Upper surface 144A with a very thin margin of 59B , lower surface 144B.

*Petioles and petiolules.*—4 to 8 cm in length and about 1.5 mm in width, round in shape, 59A to 59B in color, curly, sparsely hairy surface.

Inflorescence description:

*Inflorescence type.*—Solitary and occasionally a 3 flowered dichasial cyme.

*Inflorescence arrangement.*—Terminal.

*Peduncles.*—Up to 12 cm in length and an average of 2 mm in width, 138B heavily suffused with 59B in color, surface sparsely covered with short hairs and ribbed, bracts; simple, lanceolate in shape, up to 7 cm in length and 4 cm in width, color and surface is the same as leaflets.

*Pedicels.*—Up to 15 cm in length and an average of 2 mm in width, 138B tinted with 59B in color, surface sparsely covered with hairs.

*Bud description.*—Nodding, lanceolate in shape with tip slightly twisted, average of 5 cm in length and 1.8 cm in width, 59C in color, hairy surface and tomentose on tepal margins.

*Flower fragrance.*—None.

*Lastingness of flowers.*—Individual flowers last about 8 days, tepals drop prior to stamens.

*Flower quantity.*—About 50 flowers on a 3 year-old plant.

*Flower type.*—Star-shaped and spreading.

*Flower aspect.*—Upright facing.

*Flower size.*—Range from 8 to 16 cm in diameter and about 4 cm in depth.

*Tepal number.*—6 to 8.

*Tepal shape.*—Elliptic.

*Tepal apex.*—Acute to acuminate.

*Tepal base.*—Cuneate.

*Tepal margins.*—Entire, wavy when young becoming smooth.

*Tepal surface.*—Upper surface is glabrous, lower surface is sparsely hairy to sparsely tomentose with glabrous margin.

*Tepal color.*—Upper surface; N74D with thin margin of 71C, center N155A with veins N74C, lower surface; margin N78D with thin margin of 78C, center 157D with veins 78C.

*Tepal size.*—Up to 8 cm in length and 4 cm in width.

Reproductive organs:

*Gynoecium.*—Numerous pistils (50 to 70), 1.5 cm in length, style is 161B and plumose, stigma is 11D in color, ovary is superior and 143C in color.

*Androcoecium.*—Stamens (about 45), filaments are 0.8 to 1.3 cm in length and 0.8 mm in width, N82D in color with speckles of 155A near anther, anthers are 0.6 cm in length and 11C in color, connective is 5C in color with short obtuse tip 202A in color, pollen is moderate in quantity and 4D in color.

*Seed.*—Seed heads when pollinated is up to 5 cm in diameter and depth, achene is hairy and a blend of 138B and 59C in color, style up to 4 cm in length and 199B in color and plumose.

It is claimed:

1. A new and distinct cultivar of *Clematis* plant named 'Zoklako' as herein illustrated and described.

* * * * *